(12) United States Patent
Turowski-Wanke et al.

(10) Patent No.: US 6,180,591 B1
(45) Date of Patent: Jan. 30, 2001

(54) USE OF N-(3-DIALKYLAMINO) PROPYL-N-POLYHYDROXYALKYLCARBOXAMIDES AND THEIR ACID ADDUCTS AS THICKENERS FOR LIQUID AQUEOUS SURFACTANT SYSTEMS

(75) Inventors: Angelika Turowski-Wanke, Kelkheim; Matthias Löffler, Niedernhausen; Hans Jürgen Scholz, Alzenau; Werner Skrypzak, Lorsbach; Bernd Papenfuhs, Obertshausen, all of (DE)

(73) Assignee: Clariant GmbH, Frankfurt (DE)

( * ) Notice: Under 35 U.S.C. 154(b), the term of this patent shall be extended for 0 days.

(21) Appl. No.: 09/269,589

(22) PCT Filed: Sep. 23, 1997

(86) PCT No.: PCT/EP97/05200

§ 371 Date: May 17, 1999

§ 102(e) Date: May 17, 1999

(87) PCT Pub. No.: WO98/14543

PCT Pub. Date: Apr. 9, 1998

(30) Foreign Application Priority Data

Sep. 30, 1996 (DE) .............................. 196 40 185

(51) Int. Cl.$^7$ ...................................... C11D 3/32
(52) U.S. Cl. ............................................. 510/502
(58) Field of Search ............................... 510/502

(56) References Cited

U.S. PATENT DOCUMENTS 5,573,726 * 11/1996 Dassanayake et al. ................ 422/28

FOREIGN PATENT DOCUMENTS

| 2519088 | * | 5/1996 | (JP) . |
| 8-134496 | * | 5/1996 | (JP) . |
| 8-301828 | * | 11/1996 | (JP) . |
| 9-249683 | * | 9/1997 | (JP) . |

* cited by examiner

Primary Examiner—John Hardee
(74) Attorney, Agent, or Firm—Miles B. Dearth; Scott E. Hanf

(57) ABSTRACT

The invention relates to the use of compounds of the formula 1 as thickeners for liquid, aqueous surfactant systems

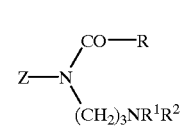

(1)

where R is an aliphatic radical having from 8 to 24 carbon atoms, $R_1$ and $R^2$, which are identical or different, are alkyl groups having from 1 to 4 carbon atoms or hydroxyalkyl groups having from 2 to 4 carbon atoms, and Z is a linear polyhydroxyhydrocarbon radical having at least 3 OH groups, which may also be alkoxylated, and also their acid addition products. The thickeners are used in industrial and standard household surfactant compositions.

14 Claims, No Drawings

USE OF N-(3-DIALKYLAMINO) PROPYL-N-POLYHYDROXYALKYLCARBOXAMIDES AND THEIR ACID ADDUCTS AS THICKENERS FOR LIQUID AQUEOUS SURFACTANT SYSTEMS

FIELD OF THE INVENTION

The production of liquid products in the cosmetics and detergent sectors is continually increasing. Particularly in the field of body cleansing compositions, it is the liquid hair shampoos, foam baths and shower preparations which have gained importance in recent years. Liquid dishwashing detergents and liquid light-duty detergents have also gained a firm place in the market.

A prerequisite for a useable liquid surfactant formulation is a long shelf life. The liquid must not cloud or form precipitations during temperature fluctuations. In addition, good tolerability by the skin is required. The product should degrease the skin as little as possible and should not lead to skin irritation.

First and foremost, however, the liquid surfactant system must also have a viscosity which is matched to the particular intended use and which can be varied as much as possible. The viscosity is thus a decisive criterion for the quality of a liquid surfactant preparation. For example, a shower gel requires very high viscosities, while a hair shampoo is usually a flowable liquid having a relatively low viscosity of from 1000 to 4000 mPas.

DESCRIPTION OF THE RELATED ART

Known thickeners for liquid surfactant formulations include nonionogenic fatty acid polyalkylene glycol esters, such as ANTIL (molecular weight about 3000, Goldschmidt AG), and, for many years now, nonionic fatty acid alkanolamides (cf. J. Amer. Oil Chem. Soc. 35, 548 (1958)). The fatty acid alkanolamide which is preferentially used in practice is coconut fatty acid diethanolamide (SUPERAMID). Compared with other fatty acid diethanolamides, it exhibits the best thickening properties.

The degree of thickening largely depends on the surfactant system and on the addition of electrolyte. Thus, it is known, for example, that sec-paraffinsulfonates as surfactants in liquid formulations present problems during viscosity adjustment. In the case of sec-paraffinsulfonates, the known currently available thickeners given above do not exhibit adequate thickening effects, even in the presence of electrolytes. EP-A-0 285 768 describes the use of N-polyhydroxyalkyl fatty acid amides as thickeners for liquid aqueous surfactant systems which, particularly in the presence of sec-paraffinsulfonates, produce a good effect.

In addition, it is known that aqueous surfactant formulations comprising fatty alcohol ether sulfates, as are often used in cosmetic formulations, can be adjusted to a desired viscosity by adding alkylamidobetaines. However, alkylamidobetaines, as byproducts, have a high sodium chloride content, which can frequently lead to corrosion during storage or processing.

Fatty acid N-alkylpolyhydroxyalkylamides and, in particular, fatty acid N-methylglucamides are nonionic surfactants which, because of their good application profile, are used, for example, for preparing detergents and cleaners. The use of these substances is the subject-matter of a large number of publications. For example, EP-A-0 285 768 describes their use as thickeners in aqueous cleaner systems. A disadvantage for the use and formulation is the limited solubility of these substances, particularly those having a chain length greater than $C_{16}$. At relatively high concentrations in water they can only be handled with difficulty because of their high viscosity. Relatively high temperatures, which reduce the viscosity, however, lead to increased hydrolysis.

It was therefore the object to find thickeners for liquid aqueous surfactant systems which satisfy the various requirements in practice with regard to surfactant, electrolyte and intended use.

DESCRIPTION OF THE PREFERRED EMBODIMENTS

Surprisingly, it has been found that compounds of the formula 1, as described in DE-A-195 12 299.2, are suitable as thickeners.

The invention provides for the use of compounds of the formula 1 as thickeners for liquid, aqueous surfactant systems

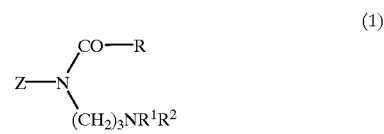

where R is an aliphatic radical having from 8 to 24 carbon atoms, $R^1$ and $R^2$, which are identical or different, are alkyl groups having from 1 to 4 carbon atoms or hydroxyalkyl groups having from 2 to 4 carbon atoms, and Z is a linear polyhydroxyhydrocarbon radical having at least 3 OH groups, which may also be alkoxylated, and also their acid addition products.

An essential advantage of the class of compounds to be used according to the invention is their high adaptability to the respective needs of the surfactant system by the possible variations in the substituents Z, R, $R^1$ and $R^2$. For example, in the class of substances according to the invention, it is possible to vary not only the fatty acid alkyl chain R, but also the hydrophobicizing substituents on the nitrogen, $R^1$ and $R^2$, and also the hydrophiling hydrocarbon radical Z. In addition, by virtue of the basic dialkylaminoalkylene radical, it is possible to influence the properties in a targeted manner by setting a certain pH.

Preference is given to compounds of the formula 1 in which R is fatty alkyl, $R^1$ and $R^2$ are methyl, and Z is the residue of a sugar alcohol derived from a reducing mono- or disaccharide, in particular from glucose.

SUMMARY OF THE INVENTION

The object of the present invention was to develop thickeners for liquid aqueous surfactant mixtures using N-(3-dialkylamino)propyl-N-polyhydroxyalkylcarboxamides and/or their acid addition products which, in addition to improved application properties such as good solubility in water, permit high surfactant concentration without organic solvents, low melting points, favorable viscosity adjustments under the various requirements in practice with regard to surfactant, electrolyte and intended use, without causing losses in performance in the detergency of the detergent mixtures.

The formulations according to the invention may comprise a compound of the formula 1 or their acid addition products as the sole surfactant, but these surfactants are preferably combined with other customary anionic, nonionic, cationic and/or amphoteric surfactants. The mixing ratio between the surfactants of the formula 1 or their acid addition products and the other surfactants can fluctuate within wide limits, for example in the weight ratio from 1 to 99 to 99 to 1, preferably from 80 to 20 to 20 to 80. The total concentration of surfactants in the formulations according to the invention can be from 1 to 99% by weight, preferably from 5 to 50% by weight.

Suitable anionic surfactants include sulfonates, sulfates, carboxylates, phosphates and mixtures of the above compounds. Suitable cations in this case are alkali metals such as, for example, sodium or potassium, or alkaline earth metals such as, for example, calcium or magnesium, and ammonium, substituted ammonium compounds, including mono-, di- or triethanolammonium cations and mixtures of the cations. The following types of anionic surfactants are of particular interest: alkyl ester sulfonates, alkylsulfates, alkyl ether sulfates, alkylbenzenesulfonates, secondary alkanesulfonates and soaps as described below.

Alkyl ester sulfonates include linear esters of $C_8$–$C_{20}$-carboxylic acids (i.e. fatty acids) which are sulfonated using gaseous $SO_3$, as described in The Journal of the American Oil Chemists' Society 52 (1975), pp. 323–329. Suitable starting materials are natural fats such as, for example, tallow, palm oil or coconut oil, but they can also be synthetic. Preferred alkyl ester sulfonates, particularly for detergent applications, are compounds of the formula

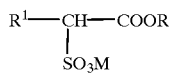

where $R^1$ is a $C_8$–$C_{20}$-hydrocarbon radical, preferably alkyl, and R is a $C_1$–$C_6$-hydrocarbon radical, preferably alkyl. M is a cation which forms a water-soluble salt with the alkyl ester sulfonate. Suitable cations are sodium, potassium, lithium or ammonium cations, such as monoethanolamine, diethanolamine and triethanolamine. $R^1$ is preferably $C_{10}$–$C_{16}$-alkyl and R is preferably methyl, ethyl or isopropyl. Particular preference is given to methyl ester sulfonates where $R^1$ is $C_{10}$–$C_{16}$-alkyl.

Alkylsulfates are in this case water-soluble salts or acids of the formula $ROSO_3M$, where R is preferably a $C_{10}$–$C_{24}$-hydrocarbon radical, preferably $C_{10}$–$C_{20}$-alkyl or hydroxyalkyl, particularly preferably $C_{12}$–$C_{18}$-alkyl or -hydroxyalkyl. M is hydrogen or a cation, e.g. an alkali metal cation (e.g. sodium, potassium, lithium), ammonium or substituted ammonium, e.g. methyl-, dimethyl- and trimethylammonium cations and quaternary ammonium cations, such as tetramethylammonium and dimethylpiperidinium cations and quaternary ammonium cations, derived from alkylamines such as ethylamine, diethylamine, triethylamine and mixtures thereof. Alkyl chains with $C_{12}$–$C_{16}$ are preferred for low wash temperatures (e.g. below about 50° C.) and alkyl chains with $C_{16}$–$C_{18}$ are preferred for higher wash temperatures (e.g. above about 50° C.).

Alkyl ether sulfates are water-soluble salts or acids of the formula $RO(A)_mSO_3M$, where R is an unsubstituted $C_{10}$–$C_{24}$-alkyl or hydroxyalkyl radical, preferably a $C_{12}$–$C_{20}$-alkyl or hydroxyalkyl radical, particularly preferably $C_{12}$–$C_{18}$-alkyl- or -hydroxyalkyl radical. A is an ethoxy or propoxy unit, m is a number greater than 0, preferably between about 0.5 and about 6, particularly preferably between about 0.5 and about 3, and M is a hydrogen atom or a cation such as, for example, sodium, potassium, lithium, calcium, magnesium, ammonium or a substituted ammonium cation. Specific examples of substituted ammonium cations are methyl-, dimethyl-, trimethylammonium and quaternary ammonium cations such as tetramethylammonium and dimethylpiperidinium cations, and those which are derived from alkylamines, such as ethylamine, diethylamine, triethylamine and mixtures thereof. Examples which may be given are $C_{12}$–$C_{18}$ fatty alcohol ether sulfates where the content of ethylene oxide is 1, 2, 2.5, 3 or 4 mol per mole of fatty alcohol ether sulfate, and where M is sodium or potassium.

In secondary alkanesulfonates, the alkyl group can either be saturated or unsaturated, branched or linear and may be substituted by a hydroxyl group. The sulfo group can occupy any position over the whole carbon chain, except that the primary methyl groups at the start and end of the chain have no sulfo groups. The preferred secondary alkanesulfonates contain linear alkyl chains having from about 9 to 25 carbon atoms, preferably from about 10 to about 20 carbon atoms and particularly preferably from about 13 to 17 carbon atoms. Examples of the preferred cation are sodium, potassium, ammonium, mono-, di- or triethanolammonium, calcium or magnesium.

Other suitable anionic surfactants are alkenyl- or alkylbenzenesulfonates. The alkenyl or alkyl group can be branched or linear and may be substituted by a hydroxyl group. The preferred alkylbenzenesulfonates contain linear alkyl chains having from about 9 to 25 carbon atoms, preferably from about 10 to about 13 carbon atoms, and the cation is sodium, potassium, ammonium, mono-, di- or triethanolammonium, calcium or magnesium and mixtures thereof. For mild surfactant systems, magnesium is the preferred cation while sodium is preferred for standard washing applications. The same applies to alkenylbenzenesulfonates.

The term anionic surfactants also includes olefinsulfonates, which are obtained by sulfonation of $C_{12}$–$C_{24}$-, preferably $C_{14}$–$C_{16}$-α-olefins with sulfur trioxide and subsequent neutralization. Owing to the preparation process, these olefinsulfonates may contain relatively small amounts of hydroxyalkanesulfonates and alkanedisulfonates. Specific mixtures of α-olefin sulfonates are described in U.S. Pat. No. 3,332,880.

Further preferred anionic surfactants are carboxylates, for example fatty acid soaps and comparable surfactants. The soaps can be saturated or unsaturated and can contain various substituents, such as hydroxyl groups or α-sulfonate groups. Preference is given to linear saturated or unsaturated hydrocarbon radicals having from about 6 to about 30 carbon atoms, preferably from about 10 to about 18 carbon atoms.

Other suitable anionic surfactants are salts of acylaminocarboxylic acids, the acyl sarcosinates obtained by reacting fatty acid chlorides with sodium sarcosinate in an alkaline medium; fatty acid-protein condensation products obtained by reacting fatty acid chlorides with oligopeptides; salts of alkylsulfamidocarboxylic acids, salts of alkyl and alkylaryl ether carboxylic acids; $C_8$–$C_{24}$-olefinsulfonates, sulfonated polycarboxylic acids prepared by sulfonation of the pyrolysis products of alkaline earth metal citrates, as described for example in GB-1,082,179; alkyl glycerol sulfates, fatty acyl glycerol sulfates, alkylphenol ether sulfates, primary paraffinsulfonates, alkylphosphates, alkyl ether phosphates, isethionates, such as acylisethionates, N-acyltaurides, alkylsuccinates, sulfosuccinates, monoesters of sulfosuccinates (particularly saturated and unsaturated $C_{12}$–$C_{18}$-monoesters) and diesters of sulfosuccinates (particularly saturated and unsaturated $C_{12}$–$C_{18}$-diesters), acylsarcosinates, sulfates of alkylpolysaccharides such as sulfates of alkylpolyglycosides, branched primary alkylsulfates and alkylpolyethoxycarboxylates such as those of the formula $RO(CH_2CH_2)_kCH_2COO^-M^+$, where R is $C_8$–$C_{22}$-alkyl, k is a number from 0 to 10 and M is a cation, resin acids or hydrogenated resin acids, such as rosin or hydrogenated rosin or tall oil resins and tall oil resin acids. Further examples are described in Surface Active Agents and Detergents (Vol. I and II, Schwartz, Perry and Berch).

Examples of suitable nonionic surfactants are the following:

Polyethylene, polypropylene and polybutylene oxide condensates of alkylphenols.

These compounds comprise the condensation products of alkylphenols having a $C_6$–$C_{20}$-alkyl group, which can be either linear or branched, with alkene oxides. Preference is given to compounds containing about 5 to 25 mol of ethylene oxide per mole of alkylphenol. Commercially available surfactants of this type are, for example, Igepal® CO-630, Triton® X-45, X-114, X-100 and X102, and the ®Arkopal-N products from Hoechst AG.

Condensation products of aliphatic alcohols with from about 1 to about 25 mol of ethylene oxide.

The alkyl chain of the aliphatic alcohols can be linear or branched, primary or secondary, and generally contains from about 8 to about 22 carbon atoms. Particular preference is given to the condensation products of $C_{10}$–$C_{20}$-alcohols with from about 2 to about 18 mol of ethylene oxide per mole of alcohol. The alkyl chain can be saturated or unsaturated. The alcohol ethoxylates can have a narrow ("narrow range ethoxylates") or a broad ("broad range ethoxylates") homolog distribution of the ethylene oxide. Examples of commercially available nonionic surfactants of this type are Teritol® 15-S-9 (condensation product of a $C_{11}$–$C_{15}$ linear secondary alcohol with 9 mol of ethylene oxide), Tergitol® 24-L-NMW (condensation product of a $C_{12}$–$C_{14}$ linear primary alcohol containing 6 mol of ethylene oxide, having a narrow molecular weight distribution). This product class also includes the Genapol® products from Hoechst AG.

Condensation products of ethylene oxide with a hydrophobic base, formed by condensation of propylene oxide with propylene glycol.

The hydrophobic part of these compounds preferably has a molecular weight of between about 1500 and about 1800. The addition of ethylene oxide to this hydrophobic part leads to an improvement in the solubility in water. The product is liquid up to a polyoxyethylene content of about 50% of the total weight of the condensation product, which corresponds to a condensation with up to about 40 mol of ethylene oxide. Commercially available examples of this product class are the Pluronic® products from BASF and the ®Genapol PF products from Hoechst AG.

Condensation product of ethylene oxide with a reaction product of propylene oxide and ethylenediamine.

The hydrophobic unit of these compounds consists of the reaction product of ethylenediamine with excess propylene oxide and generally has a molecular weight of from about 2500 to about 3000. Ethylene oxide is added onto this hydrophobic unit until the product has a content of from about 40 to about 80% by weight of polyoxyethylene and a molecular weight of from about 5000 to about 11 000. Commercially available examples of this compound class are the ®Tetronic products from BASF and the ®Genapol PN products from Hoechst AG.

Semipolar Nonionic Surfactants

This special category of nonionic compounds includes water-soluble amine oxides, water-soluble phosphine oxides and water-soluble sulfoxides, each having an alkyl radical of from about 10 to about 18 carbon atoms. Semipolar nonionic surfactants are also amine oxides of the formula

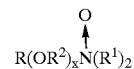

where R is an alkyl, hydroxyalkyl or alkylphenol group each having from about 8 to about 22 carbon atoms, $R^2$ is an alkylene or hydroxyalkylene group having from about 2 to 3 carbon atoms or mixtures thereof, each radical $R^1$ is an alkyl or hydroxyalkyl group having from about 1 to about 3 carbon atoms or a polyethylene oxide group having from about 1 to about 3 ethylene oxide units. The $R^1$ groups can be linked to one another via an oxygen or nitrogen atom and can therefore form a ring. Amine oxides of this type are, in particular, $C_{10}$–$C_{18}$-alkyldimethylamine oxides and $C_8$–$C_{12}$-alkoxyethyldihydroxyethylamine oxides.

Fatty Acid Amides

Fatty acid amides have the formula

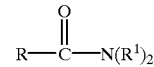

where R is an alkyl group having from about 7 to about 21, preferably from about 9 to about 17, carbon atoms, and each $R^1$ radical is hydrogen, $C_1$–$C_4$-alkyl, $C_1$–$C_4$-hydroxyalkyl or $(C_2H_4O)_xH$, where x varies from about 1 to about 3. Preference is given to $C_8$–$C_{20}$-amides, -monoethanolamides, -diethanolamides and -isopropanolamides.

Further suitable nonionic surfactants are, in particular, alkyl and alkenyl oligoglycosides and also fatty acid polyglycol esters or fatty amine polyglycol esters having in each case from 8 to 20, preferably from 12 to 18, carbon atoms in the fatty alkyl radical, alkoxylated triglycamides, mixed ethers or mixed formals, fatty acid N-alkylglucamides, protein hydrolyzates, phosphine oxides or dialkyl sulfoxides.

Typical examples of amphoteric and zwitterionic surfactants are alkyl betaines, alkylamido betaines, aminopropionates, aminoglycinates, or amphoteric imidazolinium compounds of the formula

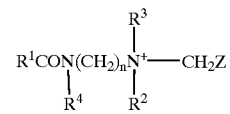

where $R^1$ is $C_8$–$C_{22}$-alkyl or -alkenyl, $R^2$ is hydrogen or $CH_2CO_2M$, $R^3$ is $CH_2CH_2OH$ or $CH_2CH_2OCH_2CH_2COOM$, $R^4$ is hydrogen, $CH_2CH_2OH$ or $CH_2CH_2COOM$, Z is $CO_2M$ or $CH_2CO_2M$, n is 2 or 3, preferably 2, M is hydrogen or a cation such as alkali metal, alkaline earth metal, ammonia or alkanolammonium.

Preferred amphoteric surfactants of this formula are monocarboxylates and dicarboxylates. Examples thereof are cocoamphocarboxypropionate, cocoamidocarboxypropionic acid, cocoamphocarboxyglycinate (also called cocoamphodiacetate) and cocoamphoacetate.

Other preferred amphoteric surfactants are alkyldimethylbetaines and alkyldipolyethoxybetaines containing an alkyl radical, which can be linear or branched, having from about 8 to about 22 carbon atoms, preferably having from 8 to 18 carbon atoms and particularly preferably having from about 12 to about 18 carbon atoms. These compounds are marketed, for example, by Hoechst AG under the trade name ®Genagen LAB.

Suitable cationic surfactants are substituted or unsubstituted straight-chain or branched quaternary ammonium salts of the type $R^1N(CH_3)_3^\oplus X^{63}$, $R^1R^2N(CH_3)_2^\oplus X^\ominus$, $R^1R^2R^3N(CH_3)^\oplus X^\ominus$ or $R^1R^2R^3R^4N^\oplus X^\ominus$. The radicals $R^1$, $R^2$, $R^3$ and $R^4$ may, preferably independently of one another, be an unsubstituted alkyl having a chain length of between 8 and 24 carbon atoms, in particular between 10 and 18 carbon atoms, hydroxyalkyl having from about 1 to about 4 carbon atoms, phenyl, $C_2$- to $C_{18}$-alkenyl, $C_7$- to $C_{24}$-aralkyl, $(C_2H_4O)_xH$, where x is from about 1 to about 3, alkyl radicals comprising one or more ester groups, or cyclic quaternary ammonium salts. X is a suitable anion.

The formulations according to the invention comprise, depending on the intended use, as well as said surfactants, also the specific auxiliaries and additives in each case. Thus, for example, detergents and cleaner formulations comprise builders, salts, bleaches, bleach activators, optical brighteners, antiredeposition agents, solubilizers and enzymes.

Customary builders are sodium aluminum silicates (zeolites), phyllosilicates, phosphates, phosphonates, ethylenediaminetetraacetic acid, nitrilotriacetate, citric acid and/or polycarboxylates.

Suitable salts or extenders are, for example, sodium sulfate, sodium carbonate or sodium silicate (water glass). Typical individual examples of other additives which may be mentioned are sodium borate, starch, sucrose, polydextrose, TAED, stilbene compounds, methylcellulose, toluenesulfonate, cumenesulfonate, long-chain soaps, silicones, mixed ethers, lipases and proteases.

As well as said surfactants, the cosmetic or pharmaceutical formulations may comprise inter alia thickeners, moisturizers, conditioners, pearlizing agents, preservatives, perfume or dyes.

Hair shampoos, hair lotions or shower preparations and bath foams may comprise, as further auxiliaries and additives, emulsifiers such as, for example, alkoxylated fatty alcohols or sorbitan esters.

The superfatting agents may be substances such as, for example, polyoxyethylated lanolin derivatives, lecithin derivatives and fatty acid alkanolamides, the latter at the same time serving as foam stabilizers.

Examples of suitable thickeners are polysaccharides, in particular xanthan gum, guar, agar agar, alginates and Tyloses, carboxymethylcellulose and hydroxyethylcellulose, also high molecular weight polyethylene glycol mono- and diesters of fatty acids, polyacrylates, polyvinyl alcohol and polyvinylpyrrolidone and also electrolytes such as common salt and ammonium chloride.

Biogenic active substances are taken to mean, for example, plant extracts and vitamin complexes.

Customary film formers are, for example, chitosan, microcrystalline chitosan, quatemized chitosan, polyvinylpyrrolidone, vinylpyrrolidone-vinyl acetate copolymers, polymers of the acrylic acid series, quaternary cellulose derivatives and similar compounds.

Another component which may be present in the formulations is a nonvolatile, liquid silicone. This can either be a polyalkylsiloxane, a polyarylsiloxane, a polyalkylarylsiloxane or a polyethersiloxane copolymer and is used in an amount of from about 0.1% to about 10.0%, preferably in an amount of from about 0.5% to about 5.0%. Mixtures of these liquids can also be used and are also advantageous for certain applications. The dispersed silicone particles should be insoluble in the shampoo matrix. The most important nonvolatile polyalkylsiloxanes which may be used are, for example, polydimethylsiloxanes having viscosities of from about 5 to about 600 000 centistokes, preferably from 350 to about 100 000 centistokes, at 25° C. A suitable essentially nonvolatile polyethersiloxane is, for example, a dimethylpolysiloxane modified using polypropylene oxide. It is also possible to use adducts containing ethylene oxide and/or propylene oxide.

Suitable silicones are described, for example, in U.S. Pat. Nos. 2,826,551, 3,946,500, 4,364,837 and in GB-849,433.

According to the invention, it is also possible to use silicone gum. Silicone gums are described in U.S. Pat. No. 4,152,416 and in product data sheets SE 30, SE 33, SE 54 and SE 76 from General Electric. "Silicone gum" is a high molecular weight polydiorganosiloxane having a molar mass of from about 200 000 to 1 000 000. Specific examples are polydimethylsiloxane, polydimethylsiloxane-methylvinylsiloxane copolymer, poly(dimethylsiloxane)-(diphenyl)(methylvinylsiloxane) copolymer and mixtures thereof; mixtures of silicone liquids and silicone gums are also suitable.

Suitable preservatives are, for example, phenoxyethanol, formaldehyde solution, parabens, pentadiol or sorbic acid.

Suitable pearlizing agents are, for example, glycol distearic acid esters, such as ethylene glycol distearate, but also fatty acid monoglycol esters.

The dyes which may be used are those substances suitable and approved for cosmetic purposes, such as, for example, those listed in the publication "Kosmetische Färbemittel" [Cosmetic Colorants] from the Farbstoffkommission der Deutschen Forschungsgemeinschaft [Dyes Commission of the German Research Society], published by Verlag Chemie, Weinheim, 1984, pp. 81 to 106. These dyes are normally used in concentrations of from 0.001 to 0.1% by weight, based on the total mixture.

The total amount of auxiliaries and additives can be from 1 to 50% by weight, preferably from 5 to 40% by weight, based on the surfactant-containing formulation.

EXAMPLES

Viscosity

The viscosity is measured using the C12/14-N-(3-dimethylamino)propyl-N-glucamide (C12/14-DMAP-GA) to be used according to the invention and the corresponding acid adducts Measuring device and conditions: Brookfield RTV-DV II viscometer, 20 rpm, 20° C.

The viscosities of binary surfactant systems consisting of lauroyl ether sulfate (LES) and C12/14-DMAP-GA were determined as a function of:
i) total DS (DS=detersive substance, given here from the sum LES+DMAP-GA)
ii) LES: DMAP-GS ratio
iii) pH
iv) NaCl content.

Ether sulfates, in particular LES, are the preferred cosurfactants.

| LES: DMAP-GA | DS [%] | pH | NaCl [%] | Viscosity [mPas] |
|---|---|---|---|---|
| 9:1 | 10 | 5 | 3.0 | 5050 |
| 8:2 | 10 | 5 | 2.0 | 4620 |
| 7:3 | 10 | 5 | 1.0 | 6150 |
| 9:1 | 10 | 6 | 3.5 | 7500 |
| 8:2 | 10 | 6 | 2.0 | 3970 |
| 8:2 | 10 | 6 | 2.5 | 7650 |
| 7:3 | 10 | 6 | 1.0 | 4130 |
| 7:3 | 10 | 6 | 1.5 | 7950 |

-continued

| LES: DMAP-GA | DS [%] | pH | NaCl [%] | Viscosity [mPas] |
|---|---|---|---|---|
| 9:1 | 10 | 7 | 3.5 | 7200 |
| 8:2 | 10 | 7 | 3.5 | 5000 |
| 8:2 | 10 | 7 | 4.0 | 7000 |
| 7:3 | 10 | 7 | 2.0 | 5100 |
| 7:3 | 10 | 7 | 2.5 | 7000 |
| 9:1 | 10 | 8 | 3.5 | 5300 |
| 8:2 | 10 | 8 | 2.5 | 4950 |
| 8:2 | 10 | 8 | 3.0 | 7550 |
| 7:3 | 10 | 8 | 2.0 | 5800 |

Table 1: Results of the viscosity measurements of binary LES/DMAP-GA surfactant systems In addition, the viscosities of binary surfactant systems consisting of alkyldiglycol ether sulfate, sodium salt (Genapol LRO), C12/C14-DMAP-GA* lactic acid, C12/C14-DMAP-GA* HCl, C16/C18-DMAP-GA* lactic acid and C16/C18-DMAP-GA* HCl were determined. The following were adjusted:
total DS (DS=detersive substance; sum of Genapol LRO and DMAP-GA acid adduct; DS=15%)
ratio of Genapol LRO: DMAP-GA acid adduct=7:3
as a function of the addition of electrolyte (NaCl)

| NaCl % | C12/C14-DMAP-GA lactic acid | C12/C14-DMAP-GA HCl | C16/C18-DMAP-GA lactic acid | C16/C18-DMAP-GA HCl |
|---|---|---|---|---|
| None NaCl | 26000 | | | Gel |
| 0.5 | | 2100 | | Gel |
| 1.0 | 15000 | 23000 | 6300 | Gel |
| 2.0 | 21000 | Gel | Gel | Gel |
| 3.0 | 12500 | Gel | Gel | Gel |
| 4.0 | | Gel | Gel | 20000 |
| 5.0 | | Gel | Gel | |
| 6.0 | | 11800 | 14000 | |
| 7.0 | | 7500 | 4500 | |

Viscosities in mPas

Table 2: Results of the viscosity measurement of binary surfactant systems of Genapol LRO/DMAP-GA acid adducts.

The test shows that the compounds used according to the invention are suitable thickeners for liquid aqueous surfactant systems; these compounds can be adjusted in a targeted manner within a broad viscosity range by varying the cosurfactant, use concentration, electrolyte content and pH, and are suitable for use in the following formulations: Liquid universal detergents, liquid light-duty detergents, manual dishwashing detergents, rinse aids, liquid cleaners and disinfectants, hair shampoos, hair rinses, hair colorants, hair-waving compositions, foam baths, face cleansers, textile and fiber auxiliaries, leather fat-liquoring agents, and auxiliaries for sludge dewatering.

The mildness to the skin of the surfactants of the formula 1 and mixtures of these surfactants with other surfactants is confirmed by determining the zein value and the red blood cell (RBC) value.

For DMAP-GA, a zein value of 39 mg of N/100 ml and an RBC value of 7% denaturatization were measured. The values correspond to very good skin compatibility.

Application Formulation Examples

Example 1

Clear Shower Gel Containing 15% Active Ingredient (Detersive Substance=DS)

Viscosity: 4140 mPas
Composition:

| A | DMAP-GA | 4.00% |
|---|---|---|
| B | Water | 48.85% |
| C | ® Genapol LRO liquid | 40.35% |
| | PEG 400 | 5.00% |
| | Perfume oil | 0.30% |
| | Preservative | q.s. |
| | Dye solution | q.s. |
| D | Citric acid | q.s. |
| E | Sodium chloride | 1.50% |

Preparation:

| I | Dissolve A in B with warming |
|---|---|
| II | Stir into I the components C one after the other |
| III | Regulate the pH using D, then adjust the viscosity using E |

Example 2

Clear Shower Gel Containing 16% Active Ingredient (DS) without Addition of Sodium Chloride Viscosity: 4750 mPas
Composition:

| A | DMAP-GA | 6.00% |
|---|---|---|
| B | Water | 54.50% |
| C | ® Genapol LRO liquid | 30.00% |
| | ® Genagen CAB 818 | 5.00% |
| | ® Hostapon KCG | 4.00% |
| | Perfume oil | 0.50% |
| | Preservative | q.s. |
| | Dye solution | q.s |
| D | Citric acid | q.s. |

Preparation: as in Example 1

Example 3

Pearlescent Shower Preparation Containing 16% Active Ingredient (DS) without Addition of Sodium Chloride Viscosity: 11,300 mPas
Composition:

| A | DMAP-GA | 6.00% |
|---|---|---|
| B | Water | 54.70% |
| C | ® Genapol LRO liquid | 35.00% |
| | ® Genapol TSM | 4.00% |
| | Perfume oil | 0.30% |
| | Preservative | q.s. |
| | Dye solution | q.s. |
| D | Citric acid | q.s. |

Preparation as in Example 1

Example 4

Clear Antidandruff Shampoo Containing 12.5% Active Ingredient DS) without Sodium Chloride Viscosity: 13,800 mPas Composition:

| A | DMAP-GA | 5.00% |
|---|---|---|
|   | ® Octopirox | 0.50% |
| B | Water | 64.20% |
| C | ® Genapol LRO liquid | 30.00% |
|   | Perfume oil | 0.30% |
|   | Preservative | q.s. |
|   | Dye solution | q.s. |
| D | Citric acid |  |

Preparation as in Example 1

Example 5
Clear Antidandruff Shampoo Containing 12.5% Active Ingredient (DS)
Viscosity: 4010 mPas
Composition:

| A | DMAP-GA | 2.50% |
|---|---|---|
|   | ® Octopirox | 0.50% |
| B | Water | 57.10% |
| C | ® Genapol LRO liquid | 30.00% |
|   | ® Medialan LD | 6.60% |
|   | Perfume oil | 0.30% |
|   | Preservative | q.s. |
|   | Dye solution | q.s. |
| D | Citric acid | q.s. |
| E | Sodium chloride | 3.00% |

Preparation as in Example 1

Example 6
Clear Antidandruff Shampoo Containing 12.5% Active Ingredient (DS)
Viscosity: 9000 mPas
Composition:

| A | DMAP-GA | 2.50% |
|---|---|---|
|   | ® Octopirox | 0.50% |
| B | Water | 61.35% |
| C | ® Genapol LRO liquid | 30.00% |
|   | ® Genapol SBE | 3.35% |
|   | Perfume oil | 0.30% |
|   | Preservative | q.s. |
|   | Dye solution | q.s. |
| D | Citric acid | q.s. |
| E | Sodium chloride | 2.00% |

Preparation as in Example 1

Example 7
Clear Hair Shampoo Containing 15% Active Ingredient (DS)
Viscosity: 5100 mPas
Composition:

| A | DMAP-GA | 5.00% |
|---|---|---|
| B | Water | 53.70% |
| C | ® Genapol LRO liquid | 35.00% |
|   | ® Genapol SBE | 5.00% |
|   | Perfume oil | 0.30% |
|   | Preservative | q.s. |
|   | Dye solution | q.s. |

-continued

| D | Citric acid | q.s. |
|---|---|---|
| E | Sodium chloride | 1.00% |

Preparation as in Example 1

Example 8
Clear Dishwashing Detergent Containing 32.5% Active Ingredient (DS) without Addition of Chloride
Viscosity: 880 mPas
Composition:

| A | DMAP-GA | 5.00% |
|---|---|---|
| B | Water | 53.70% |
| C | ® Genapol LRO liquid | 6.00% |
|   | ® Hostapur SAS 60 | 35.00% |
|   | Perfume oil | 0.30% |
|   | Preservative | q.s. |
|   | Dye solution | q.s. |
| D | Citric acid | q.s. |

Preparation as in Example 1

Example 11
Pearlescent Shower Preparation, 14% DS
Viscosity: 9100 mPas
Composition:

| A | ® GENAPOL LRO liquid (Hoechst AG) | 35.00% |
|---|---|---|
| B | C12/14-DMAP-GA × lactic acid (Hoechst AG) | 7.60% |
|   | ® GENAPOL PGL (Hoechst AG) | 4.00% |
|   | Perfume oil | 0.30% |
|   | Water | 53.10% |
|   | Preservative | q.s. |
|   | Dye solution | q.s. |
| C | Lactic acid | q.s. |

Preparation

| I | Stir into A the components of B one after the other. |
|---|---|
| II | Regulate the pH using C. |

Example 12
Clear Shower Gel, 14% DS
Viscosity: 12400 mPas
Composition:

| A | ® GENAPOL LRO liquid (Hoechst AG) | 30.00% |
|---|---|---|
| B | C12/14-DMAP-GA × hydrochloric acid (Hoechst AG) | 8.40% |
|   | ® GENAGEN CAB 818 (Hoechst AG) | 5.00% |
|   | Perfume oil | 0.30% |
|   | Water | 56.30% |
|   | Preservative | q.s. |
|   | Dye solution | q.s. |
|   | Hydrochloric acid | q.s. |

Preparation

| I Stir into A the components of B one after the other. |
| II Regulate the pH using C. |

Example 13
Clear Antidandruff Shampoo, 14% DS
Viscosity: 12600 mPas
Composition:

| A ® OCTOPIROX (Hoechst AG) | 0.50% |
| B ® GENAPOL LRO liquid (Hoechst AG) | 35.00% |
| C C12/14-DMAP-GA × hydrochloric acid (Hoechst AG) | 8.40% |
| Perfume oil | 0.30% |
| Water | 55.80% |
| Preservative | q.s. |
| Dye solution | q.s. |
| D Hydrochloric acid | q.s. |

Preparation

| I Dissolve A in B. |
| II Stir into I the components of C one after the other. |
| III Regulate the pH using D. |

Example 14
Clear Hair Shampoo, 14% DS
Viscosity: 6600 mPas
Composition:

| A ® GENAPOL LRO liquid (Hoechst AG) | 35.00% |
| B C12/14-DMAP-GA × lactic acid (Hoechst AG) | 7.60% |
| Perfume oil | 0.30% |
| Water | 57.10% |
| Preservative | q.s. |
| Dye solution | q.s. |
| C Lactic acid | q.s. |

Preparation

| I Stir into A the components of B one after the other. |
| II Regulate the pH using C. |

Example 15
Universal Detergent
Composition:

| Alkylsulfate | 12% |
| Soap | 1% |
| Fatty alcohol oxethylate | 4% |
| DMAP-GA | 3% |
| Sodium carbonate | 6% |
| Filosilicate SKS-6 | 14% |
| Zeolite | 14% |
| Sodium citrate | 5% |
| Sodium sulfate | 2% |

*-continued*

| Sodium percarbonate | 20% |
| Bleach activator | 4% |
| Polyacrylate (CP-5) | 6% |
| Enzymes | 1% |
| Water | ad 100% |

Example 16
Light-duty Detergent
Composition:

| Alkylbenzenesulfonate | 14% |
| Alkylsulfate | 8% |
| Soap | 2% |
| Fatty alcohol ethoxylate | 4% |
| DMAP-GA | 2% |
| Sodium carbonate | 1% |
| Filosilicate SKS-6 | 5% |
| Zeolite | 40% |
| Sodium sulfate | 14% |
| Enzymes | 1% |
| Water | ad 100% |

List of Commercial Products Used

| ® Genapol LRO liquid | $C_{12}/C_{18}$-alkyl diglycol ether sulfate, sodium salt (about 27% DS) |
| ® Hostapur SAS 60 | Secondary alkanesulfonate, sodium salt (about 60% DS) |
| ® Genapol SBE | $C_{12}/C_{18}$-alkylpolyglycol ether sulfosuccinate, disodium salt (about 40% DS) |
| ® Medialan LD | Fatty acid sarcoside, sodium salt (about 30% DS) |
| ® Genapol TSM | Alkyl ether sulfate and pearlizing agents |
| ® Genapol OA 080 | $C_{12}/C_{14}$-fatty alcohol ethoxylate containing 8 EO |
| ® Genagen CAB 818 | Alkylamidopropylbetaine (about 30% DS) |
| ® Hostapon KCG | N-cocoylglutamic acid, monosodium salt (about 25% DS) |
| PEG 400 | Polyethylene glycol (molar mass about 400) |
| ® Octopirox | 1-Hydroxy-4-methyl-6-(2,4,4-trimethylpentyl)-2(1H)pyridinone, 2-aminoethanol salt (antidandruff agent) |

What is claimed is:

1. A method for thickening a liquid aqueous surfactant system comprising adding a compound of the formula 1 to said liquid aqueous surfactant system

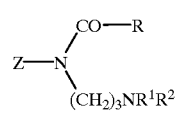 (1)

wherein R is an aliphatic radical having from 8 to 24 carbon atoms, $R^1$ and $R^2$, which are identical or different, are alkyl groups having from 1 to 4 carbon atoms or hydroxyalkyl groups having from 2 to 4 carbon atoms, and z is a linear polyhydroxyhydrocarbon radical having at least 3 OH groups, which may also be alkoxylated, and also their acid addition salts.

2. The method as claimed in claim 1, wherein R is fatty alkyl, $R^1$ and $R^2$ are methyl, and Z is the residue of a sugar alcohol derived from a reducing mono- or disaccharide.

3. The method as claimed in claim 2, wherein the reducing monosaccharide is glucose.

4. The method as claimed in claim 1, wherein they are present in the surfactant system in an amount of from 0.5 to 30% by weight, based on the total liquid surfactant system.

5. The method as claimed in claim 1, wherein one or more anionic, cationic, nonionic and/or amphoteric surfactants are additionally used.

6. The method as claimed in claim 1, wherein ether sulfates are additionally used.

7. The method as claimed in claim 6, wherein the ether sulfate is lauroyl ether sulfate.

8. A product selected from the group consisting of a liquid light-duty detergent, universal detergent, manual dishwashing detergent, rinse aid, liquid detergent and disinfectant, syndet soap, hair shampoo, hair rinse, hair colorant, hair-waving composition, foam bath, face cleaner, textile and fiber auxiliary, leather fat-liquoring agent, floatation auxiliary and auxiliary for sludge dewatering, which comprises an aqueous surfactant system containing compounds of the formula 1

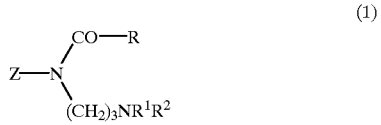

(1)

where R is an aliphatic radical having from 8 to 24 carbon atoms $R^1$ and $R^2$, which are identical or different, are alkyl groups having from 1 to 4 carbon atoms or hydroxyalkyl groups having from 2 to 4 carbon atoms, and z is a linear polyhydroxyhydrocarbon radical having at least 3 OH groups, which may also be alkoxylated, including their acid addition salts.

9. The product of claim 8 wherein R is a fatty alkyl, $R^1$ and $R^2$ are methyl, and z is the residue of a sugar alcohol derived from a reducing mono- or disaccharide.

10. The product of claim 9 wherein said sugar alcohol is derived from glucose.

11. The product of claim 8 wherein compounds of the formula 1 are present in said liquid surfactant system in an amount of from 0.5 to 30% by weight, based on the total weight of said liquid surfactant system.

12. The product of claim 8 wherein said surfactant system further comprises one or more anionic, cationic, nonionic and/or amphoteric surfactants.

13. The product of claim 12 further comprising said anionic surfactant which is an ether sulfate.

14. The product of claim 13 wherein said ether sulfate is lauroyl ether sulfate.

* * * * *